United States Patent [19]
Schmitt et al.

[11] Patent Number: 5,503,636
[45] Date of Patent: Apr. 2, 1996

[54] SELF-EXPANDING STENT FOR HOLLOW ORGANS

[75] Inventors: Klaus Schmitt, Remshalden-Grunbach; Armin Singvogel, Remseck; Helmuth Entenmann, Schorndorf-Schornbach; Mogens Amstrup, Schorndorf, all of Germany; Walter Klepetiko, Vienna, Austria

[73] Assignee: Willy Rusch AG, Germany

[21] Appl. No.: 249,724

[22] Filed: May 26, 1994

[51] Int. Cl.$^6$ .................................. A61M 29/02
[52] U.S. Cl. ................. 606/200; 623/1; 623/12; 606/194
[58] Field of Search ............... 606/191, 198, 606/200; 128/899; 604/104–106; 623/1, 12

[56] References Cited

U.S. PATENT DOCUMENTS

| | | |
|---|---|---|
| 4,434,797 | 3/1984 | Silander . |
| 4,733,665 | 3/1988 | Palmaz . |
| 5,015,253 | 5/1991 | MacGregor .................. 623/1 |
| 5,122,154 | 6/1992 | Rhodes . |
| 5,123,917 | 6/1992 | Lee ............................. 623/1 |
| 5,141,502 | 8/1992 | Malcaluso, Jr. . |
| 5,222,971 | 6/1993 | Willard et al. ............... 606/200 |
| 5,234,456 | 8/1993 | Silvestrini ..................... 623/1 |
| 5,258,027 | 11/1993 | Berghaus ...................... 623/12 |

FOREIGN PATENT DOCUMENTS

| | | |
|---|---|---|
| 0177330 | 4/1986 | European Pat. Off. . |
| 0221570 | 5/1987 | European Pat. Off. . |
| 0556850 | 8/1993 | European Pat. Off. . |
| 2694688 | 2/1994 | France . |
| 1766921 | 1/1970 | Germany . |
| 2546283 | 5/1976 | Germany . |
| 9101344.5 | 6/1991 | Germany . |
| 1205743 | 9/1970 | United Kingdom . |
| 2189150 | 10/1987 | United Kingdom . |
| WO83/00997 | 3/1983 | WIPO . |
| WO91/12779 | 9/1991 | WIPO . |

*Primary Examiner*—Stephen C. Pellegrino
*Assistant Examiner*—William Lewis
*Attorney, Agent, or Firm*—Walter A. Hackler

[57] ABSTRACT

A stent for the splinting and/or for the holding open of a hollow organ is comprised from filaments 11 which are formed together into a tubular and self-expanding netting. In the collapsed state the stent 10 is stretched in an axial direction and in an extended state the stent is fore-shortened in the axial direction. The filaments 11 are formed with rectangular cross-section and the crossing-points 12 are securely attached to another at the free ends 14 and 15.

11 Claims, 3 Drawing Sheets

SELF-EXPANDING STENT FOR HOLLOW ORGANS

BACKGROUND OF THE INVENTION

The invention concerns a stent for the splinting and/or for the holding open of a hollow organ, with a tubular and self-expandable netting made from filaments, which, in a collapsed state, extends in an axial direction and in an extended state is shortened in the axial direction.

A stent of this kind has become known in the arm through EP 0 177 330 B1.

Stents of the known kind are, for example utilized for the treatment of vessel illnesses. Stents allow a vessel lumen to be permanently held open through their transluminal implantation. With the assistance of interventional radiology it is thereby possible to complement invasive surgery or, in an advantageous case, to render same unnecessary. The transluminal utilization of stents for the splinting or for the permanent extending of stenoses is particularly advantageous in patients with high surgical risk factors.

In addition to metallic memory protheses, which are made from nitinol wire, double helix spirals are known in the art for splinting and for keeping open a narrowing in a vessel which open a narrowed lumen in that they, by means of a known insertion instrument, are introduced into the appropriate location of the vessel and expanded in place. The double helix spiral is held in place via its own expanding forces against the wall of the vessel.

Also known is a "Palmaz-stent" which comprises a thin-wall tube made from rust-free steel and exhibiting longitudinal slits. The tube-shaped stent is mounted, for purposes of insertion, onto a dilating balloon and through insufflation of the balloon, is expanded and released in place. A net-like structure is formed by the expansion of the tube shaped stent.

The stent known from EP 0 177 330 B1 comprises a steel wire which is shaped in a zig-zag form. When pressed together it is possible to insert the stent through a catheter placed in the vessel whereby after expulsion, the stent automatically expands under its own forces. The internal forces of the known stent can be varied through the choice of the strength of the rounded wire, the degree of pre-bending, and the number of zig-zag bends. A disadvantage of this system, is possible breakage due to material fatigue of the round wire in the vicinity of the particularly highly stressed "Z-portions".

It is the underlying purpose of the invention to further improve a self-expanding stent of the above mentioned kind in that, by means of improved expansion behaviour, as protective a seating as possible of the filaments on the inner walls of the hollow organ is guaranteed and a removal of the inserted stent is made, in a simpler fashion, possible.

SUMMARY OF THE INVENTION

This purpose is accomplished in accordance with the invention in that the filaments are configured with rectangular shaped cross-sections and are attached to each other at crossing-points of the stent.

Thereby, the inventive stent has the advantage that it can exhibit, in its collapsed state, a smaller diameter than the known self-expanding stents made from round filaments. Preferably, a flat metallic band, which is substantially wider than it is high, is utilized as filament in the inventive stent. In this fashion, the inventive stent seats areally on the inside wall of the hollow organ and the filaments press protectively in a non-line-shaped fashion into the inner wall which is to be expanded. In addition the netting-like stent can be manufactured from a reduced number of filaments compared to the known stent. A simplified and reproducible manufacture of the inventive stent is also achieved, since it can be woven or interlaced in a simple and apparent fashion. The position of the individual and of the wound filaments can be optically traced in a simple fashion along the entire length of the stent.

Furthermore, the crossing-points can be attached to each other in a simple and defined fashion because an areal seating of the filaments takes place at the crossing-points. An undefined twisting together of the ends of the filaments and thereby, as with known stents, an enlargement of the end regions with the neighboring vessel tissue cannot take place with the inventive stent because the individual ends of the filaments are fixed to each other. It is furthermore advantageous that the areal filaments are easily detected with x-rays and the entire position of the inserted stent is clearly discernible. If a fixed crossing-point is located at each end of the inventive stent, when removal of the inventive stent is desired, it is possible for the stent to be extended and, in a known fashion, also be removed from the vessel or from the hollow organ in the manner in which it was introduced.

Flat-band filaments have proved themselves as construction elements for the inventive stent. If a flat steel band is utilized for the production of the inventive stent, which is significantly wider than it is high, the stent, in the stretched state, is thereby extremely thin and thereby, by means of extremely thin insertion instruments, can be safely introduced and located either percutaneously or through the lumen of the hollow organ. The introduction and situating as well as the self-expansion in the hollow organ or in the vessel are thereby rendered extremely easy. In its expanded state, the stent seats areally at the inside wall of the hollow organ. The danger of perforation of the hollow organ wall is reduced by the areal seating of the individual filaments.

Furthermore, the inventive stent exhibits a large variability in cross-section, in length and in expansion strength with increased longitudinal flexibility. This is achieved in that, with a flat band, the differently directed force components also exhibit different magnitudes. In a round wire, the resulting force components are always of equal magnitude since, with a circularly cross-sectioned filament, the forces emanating from the material are not substantially different. It is thereby possible for the inventive stent to adjust to the most different of paths in the hollow organ. Through the areal seating on the inner wall of the hollow organ which is to be expanded, the risks of thrombosis and of a possibly severe intimal hyperplasia are reduced in the vicinity of the ends of the stent.

In a preferred embodiment of the invention, the filaments are surrounded by a rubber elastic plastic material. This contributes to an improved biological comparability. Depending on the choice of the rubber elastic material, the restoring forces of the stent can be increased to a greater or lesser degree. Furthermore, the crossing-points are fixed in a defined fashion by the plastic jacketing.

In the stretched state of the inventive stent, open areas are formed between the filaments which can be filled by a rubber elastic material. The rubber elastic layer is formed on the outer and inner periferal surfaces of the stent. Thereby a tissue swelling and a new narrowing of the hollow organ is prevented.

In the inventive stent, the filaments can be woven or intertwined, against the fundamental bending sense, into a tubular netting. This has the advantage that the flexibility and the expansion pressure, e.g. the internal forces of the inventive stent, can be varied in a defined fashion by means of a variation of the density of the netting and by the choice of flat band (metal, type, width, height).

In a further embodiment of the invention the individual filaments are provided with, in addition to a plastic rubber elastic surface layer, an additional hydrophilic surface layer. This provides for improved flow values in the hollow organ at the expanded location.

The inventive stent can be inserted with a known insertion instrument and is arranged in this insertion instrument in a detachable fashion. This has the advantage that already existing insertion instruments can also be utilized for the insertion of the inventive stent.

Further advantages can be derived from the description and the accompanying drawing. The above mentioned features and those which are to be described below can likewise, in accordance with the invention, each be utilized individually or collectively in arbitory combination. The embodiments mentioned are not to be considered as exhaustive enumeration, but rather have exemplary character only. The invention is represented in the drawing and explained by means of the embodiments.

BRIEF DESCRIPTION OF THE DRAWINGS

FIG. 1b shows a cross-section in accordance with Ib—Ib of FIG. 1a;

DESCRIPTION OF THE PREFERRED EMBODIMENT

Figure 1:
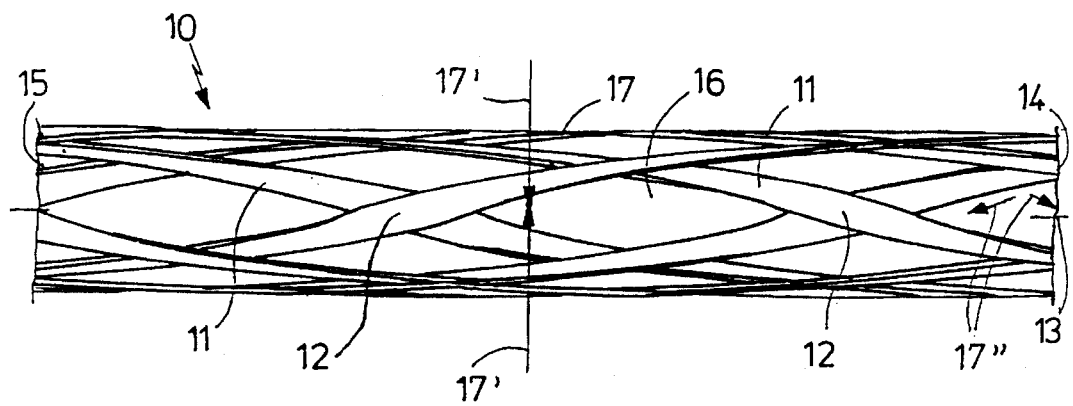
FIG. 1 shows a stent in accordance with the invention in the stretched state with filaments jacketed in plastic and with contained free spaces.

The individual figures of the drawing show the inventive object in a partially largely schematized fashion and are not to be taken to scale. The objects in the individual drawings are shown in a greatly enlarged fashion so that their construction can be more easily illustrated.

10 of FIG. 1 shows a partially collapsed stent which is formed from filaments 11 (two filaments are labeled with the reference symbol 11 in the drawing) which are made from flat wire bands. The flat wire bands exhibit, for example, a width of 0.075 mm and are 0.005 mm thick. The flat metal bands are, for example, manufactured from rust-free steel. The filaments 11 seat upon each other at the crossing-points 12 and, together, exhibit twice the height of an individual filament 11. The filaments 11 lie in areal contact upon each other at the crossing-points 12. A plurality of filaments 11 are woven into a tubular netting which forms stent 10. The filaments 11 stretch longitudinally relative to an axis 13. The crossing-points 12 are so configured at the free ends 14, 15 that the individual overlapping filaments 11 are securely attached to each other. Rhombic-shaped free spaces 16 are formed between the individual filaments 11 which, depending on the state of stretching or extension of the stent 10, can be larger or smaller. In FIG. 1, the free spaces 16 are filled in with a rubber elastic material 17. It is possible to additionally influence the flexibility and the expansion forces of the stent 10 by means of the rubber elastic material. Depending on the compressional state, the rubber elastic plastic material in the free spaces 16 is compressed and, in the outer region, the rubber elastic material 17 is subjected to a tensil force. The compression of the rubber elastic material is indicated with arrow 17' in FIG. 1 and the tensil force is represented by the arrow 17". Depending on the choice of the rubber elastic material 17 it is possible to increase or decrease the restoring forces of the inventive stent 10. The filaments 11, via their metallic surfaces, lie on top of each other at the crossing-points 12 and the entire crossing-point 12 is surrounded in plastic.

Figure 1A:
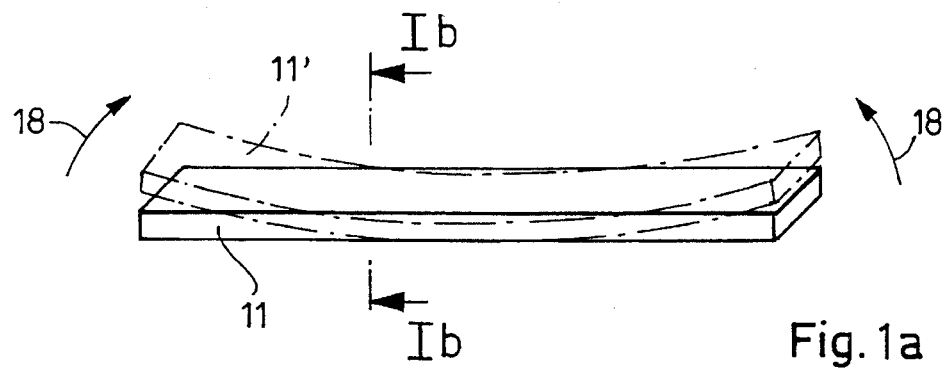
FIG. 1a shows an individual filament made from a flat metal band in straight, flat as well as in bent extension.

FIG. 1a shows a filament 11 as it would be utilized in a plurality of windings in the stent 10 of FIG. 1. The filament 11 is a flat steel band exhibiting a rectangular shape and having a fundamental bend which is indicated by the dashed lines in the figure. The filament 11, due to the manufacturing procedure, is bent in the direction of the arrow 18 into an element 11'.

Figure 1B:
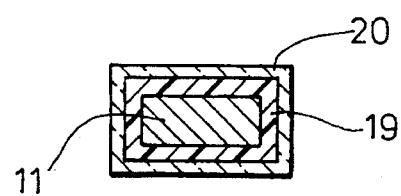

FIG. 1b shows a cut Ib—Ib of FIG. 1a. The filament 11, a flat steel band, is completely jacketed by an elastic plastic material 19. Furthermore, the elastic plastic material 19 is completely enclosed by a hydrophilic layer 20 which, depending on need, is used in the various embodiments of the inventive stent. It can also be advantageous if the elastic plastic material 19 has recesses at the seating locations of the crossing-points of the individual filaments 11, so that the entire thickness of the netting is reduced at the crossing-points 12.

Figure 2:
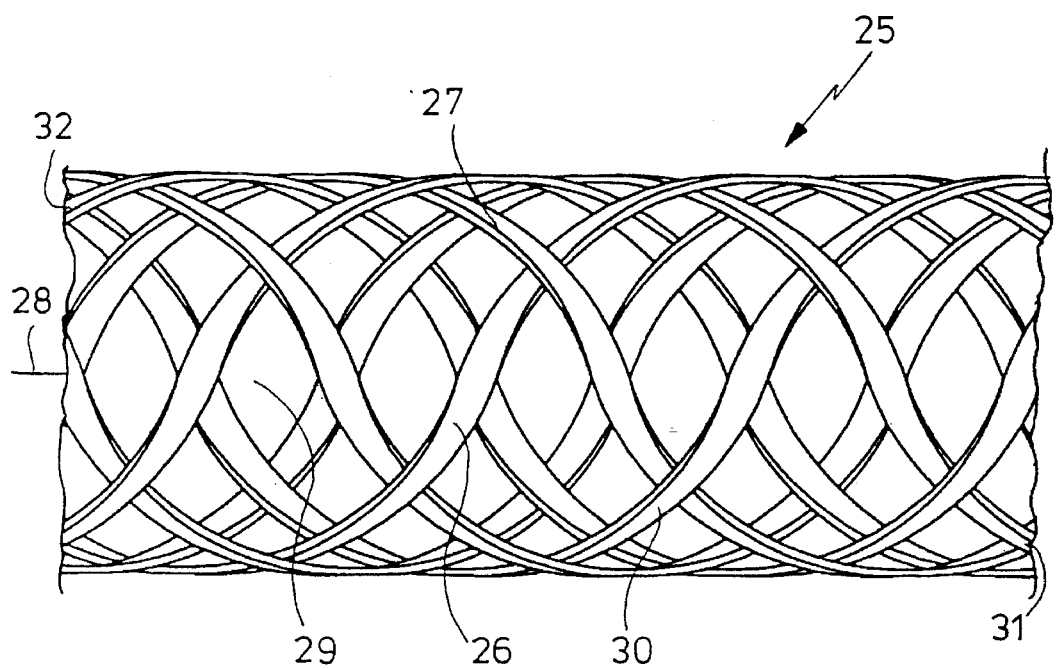
FIG. 2 shows a section of the stent in the extended state with crossing-points which are joined together in a hinged fashion.

FIG. 2 shows a section of a stent 25 in the extended final state. Filaments 26 are extended in a fashion commensurate with their internal forces and are rotated at the crossing-points 27 in such a fashion that free spaces 29 form which are factors larger than, for example, the free spaces 16 illustrated in FIG. 1. The stent section 25 is shortened relative to an access 28 and the hinge-like connection with which the individual crossing-points 27 of the filaments 26 are held together is indicated with 30. The filaments 26 are completely jacketed at the crossing-points and, within the jacketed layer, it is possible for the filaments 26 to hingingly move relative to another. Depending on which material is chosen for the jacketing, it is possible to strengthen a restoring force from the collapsed state of the inventive stent to the extended state. In the final position as, for example, shown in FIG. 2, the stent, in the stretched state, exhibits an outer diameter of approximately 3 mm to approximately 30 mm. The size of the final position depends on the strength of the flat metal bands used, the method of interlacing or weaving, and the fashion in which the plastic jacketing of the individual filaments 26 is carried out. The stent section 25 is shortened in the longitudinal sense relative to an axis 28 in the extended state. The free ends of the stent 25 are labeled with the reference symbols 31, 32 in the figure.

Figure 3:
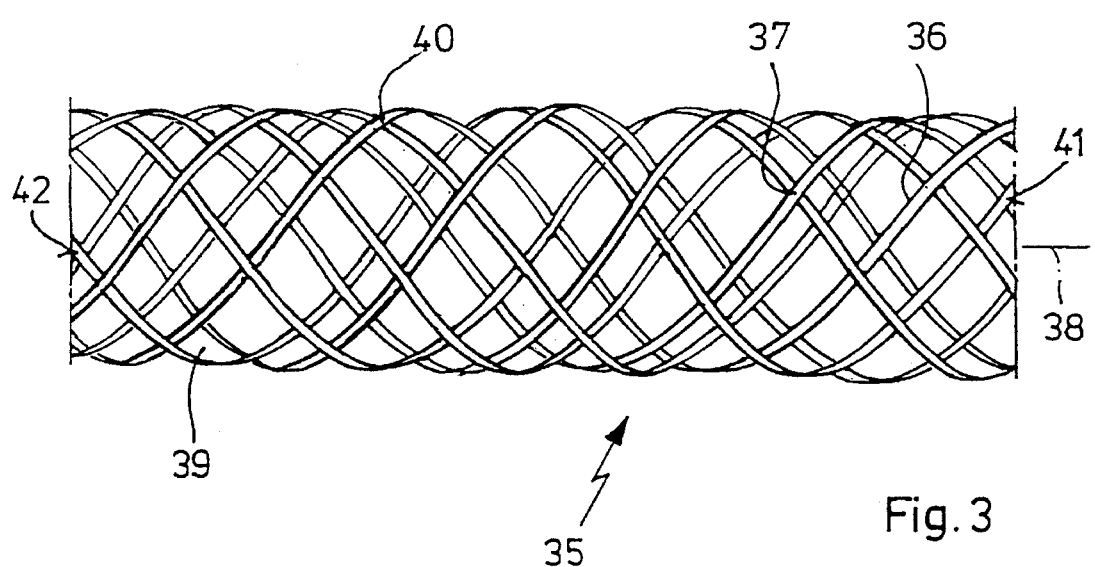
FIG. 3 shows a further embodiment of a section of the stent in the extended state with connecting crossing-points formed from overlapping filaments.

FIG. 3 shows a further embodiment of a section 35 of a stent in the extended state. Thereby, the filaments 36, which exhibit rectangular cross-sections, are woven into a tubular netting. The filaments 36 cross each other at the crossing-points 37. Relative to a collapsed state of the stent section 35, which is not shown in FIG. 3, the stent section 35 of the figure is longitudinally shortened along the axis 38. The bordering sections of the filament 36 adjoin free spaces 39 which exhibit rhombic shapes and which can push into the bordering tissue of the hollow organ. 40 indicates a joint at which the individual filaments 36 freely lie on top of each other. Due to the internal forces in the netting-like weave, the individual filaments 36 press against each other. The internal forces are predetermined in the stent, so that the tubular netting goes into a well-defined final state through a radial enlargement. In the extended state one constant lumen width is always maintained. Towards this end, the inventive stent adjusts to motions, which are radially or longitudinally directed, in the best possible fashion. Free ends of the stent 35 are labeled with 41, 42. The filaments 36 are securely connected to each other in the vicinity of the free ends 41, 42 at the crossing-points 37.

Figure 3A:
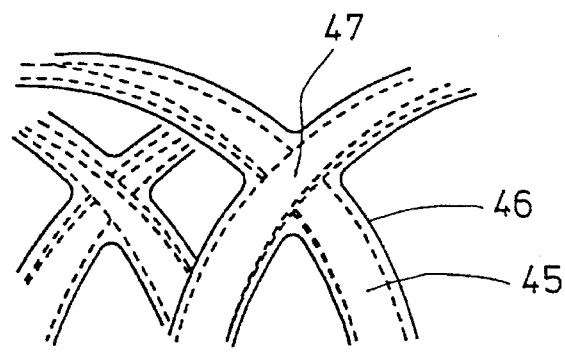
FIG. 3a shows a sectional enlargement of a stent in the self-expanding state at the crossing-points.

FIG. 3a shows filaments 45 which are jacketed by a plastic 46 exhibiting rubber elastic properties. Thereby, the filaments 45 are represented by dashed lines. The filaments 45 lie on top of each other via their metallic surfaces at the crossing-points 47 and the mutually crossing filaments 45 are, in their entirety, jacketed in plastic so that a fixed joint is formed at the crossing-point 47. FIG. 3a shows the crossing-point 47 in a self-expanded state. Herein, the plastic 46 jacketing the crossing-point 47 is nearly force-free.

Figure 3B:
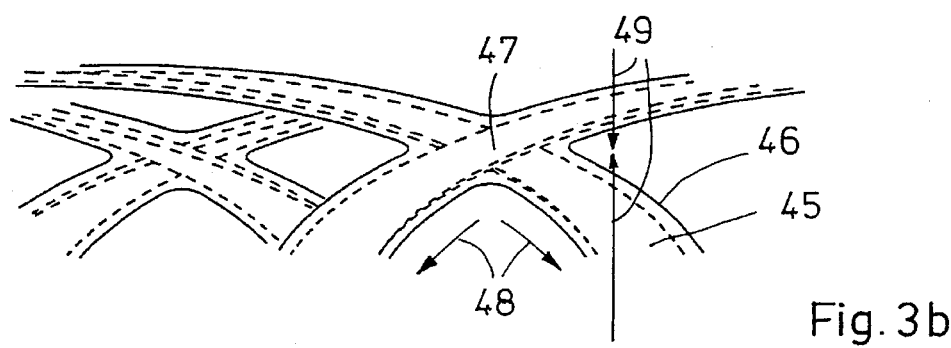
FIG. 3b shows a sectional enlargement of a stent in the active, longitudinally stretched state at the crossing-points.

FIG. 3b shows the filaments 45 with a plastic jacketing 46 in the active longitudinally stretched state. At crossing-point 47 the plastic is stretched in the direction of the arrow 48 and compressed in direction of the arrow 49.

Figure 4:
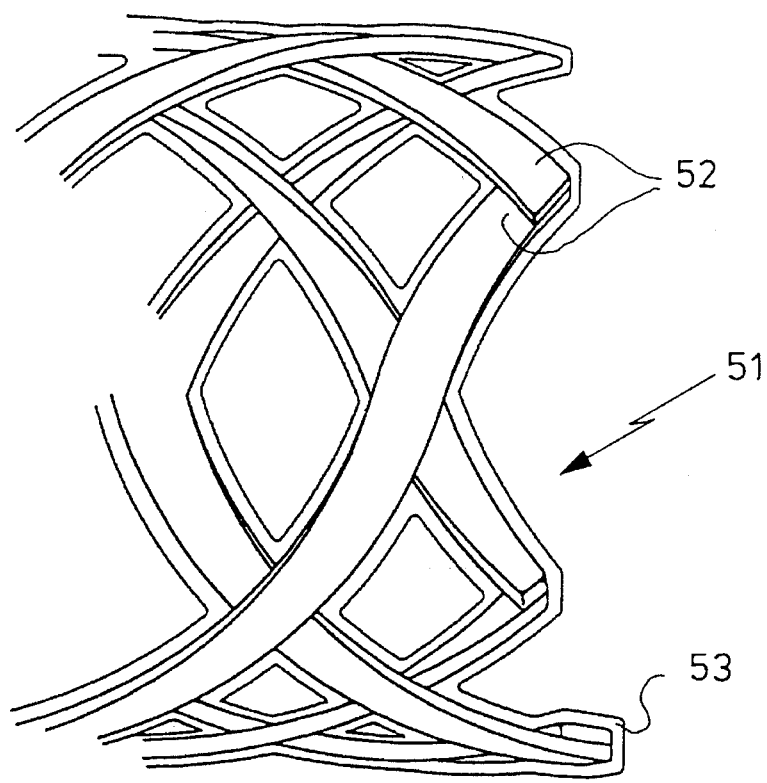
FIG. 4 shows a stent in the vicinity of a free end.

FIG. 4 shows a free end 51 of an inventive stent. Hereby, the free ends of filaments 52 lie fixed upon each other in that they are jacketed by plastic as indicated with the reference symbol 53. The overlaps could however also be, for example, additionally secured to each other by soldering. The areal seating provides for a secure attachment. A glueing of the mutually crossing filaments is also conceivable.

The stent shown in FIG. 1 to 4 is easily detected by means of x-rays and can thereby be clearly identified.

A stent for the splinting and/or the holding open of a hollow organ comprises filaments 11 which are joined into a tubular and self-expanding network. In the collapsed state the stent 10 is stretched in the axial direction and in the extended state the stent 10 is shortened in the axial direction. The filaments 11 are rectangularly formed in cross-section and the crossing-points 12 are connected securely to another at the free ends 14 and 15.

We claim:

1. Stent for at least one of splinting and holding open a hollow organ comprising filaments woven into a tubular self-expanding meshwork, the filaments having rectangular shaped cross sections and weavingly overlapping at crossing points, and also comprising an elastic plastic jacketing encasing the crossing points to form a fixed joint thereon, whereby, in a collapsed state, the stent is stretched in an axial direction and, in a expanded state, is shortened in the axial direction, the stent further comprising a hydrophilic layer integral with the filaments.

2. The stent of claim 1, wherein the filaments are metal.

3. The stent of claim 1, wherein the elastic plastic jacketing encases the filaments.

4. The stent of claim 1, wherein the meshwork has free spaces formed between the filaments in both the collapsed and expanded states, the free spaces being spanned by an elastic material.

5. The stent of claim 1, wherein the filaments exhibit an intrinsic bend direction and are woven into the tubular meshwork to curve in a direction opposite to the intrinsic bend direction.

6. Stent for at least one of splinting and holding open a hollow organ comprising a first tube helically wound in a first winding direction from a first filament having rectangular cross section; a second tube helically wound in a second winding direction from a second filament having rectangular cross section, the first and the second filaments being woven through another to form a self-supporting meshwork having crossing points defining rhombic-shaped openings in an outer cylindrical surface; and an elastic plastic jacketing encasing the crossing points to form a fixed joint thereon, whereby, in a collapsed state, the stent is stretched in an axial direction and, in an expanded state, is shortened in the axial direction, the stent further comprising a hydrophilic layer integral with the filaments.

7. Stent for at least one of splinting and holding open a hollow organ comprising filaments woven into tubular self-expanding meshwork having a longitudinal cylindrical surface and two ends, the filaments having rectangular shaped cross sections and weavingly overlapping to form crossing points along the longitudinal surface and at the two ends, and also comprising an elastic plastic jacketing encasing the crossing points to form a fixed joint thereon, whereby, in a collapsed state, the stent is stretched in an axial direction and, in an expanded state, is shortened in the axial direction, the stent further comprising a hydrophilic layer integral with the filaments.

8. The stent of claim 6, wherein the filaments exhibit an intrinsic bend direction and are woven into the tubular meshwork to curve in a direction opposite to the intrinsic bend direction.

9. The stent of claim 7, wherein the filaments exhibit an intrinsic bend direction and are woven into the tubular meshwork to curve in a direction opposite to the intrinsic bend direction.

10. Stent for at least one of splinting and holding open a hollow organ comprising filaments woven into a tubular self-expanding meshwork, the filaments having rectangular shaped cross sections and weavingly overlapping at crossing points having elastic fixed joints therebetween, the stent further comprising a hydrophilic layer integral with the filaments.

11. The stent of claim 10 wherein the crossing points are encased by an elastic plastic jacketing.

* * * * *